United States Patent [19]

Hirose et al.

[11] Patent Number: 5,476,573
[45] Date of Patent: Dec. 19, 1995

[54] APPARATUS FOR DEFOAMING AND CONTROLLING AEROBIC CULTURE FERMENTATION

[75] Inventors: Toshiki Hirose, Kawasaki; Koji Shimazaki, Saga; Takashi Nakamura, Kawasaki; Atsuo Shiraishi, Kawasaki; Hiroki Kawashima, Kawasaki; Tatsuya Nakayama, Kawasaki, all of Japan

[73] Assignee: Ajinomoto Co., Inc., Tokyo, Japan

[21] Appl. No.: 980,291

[22] Filed: Nov. 23, 1992

[30] Foreign Application Priority Data

Nov. 22, 1991 [JP] Japan .................................. 3-307613

[51] Int. Cl.$^6$ ................................................ C12M 1/21
[52] U.S. Cl. .................... 202/197; 202/264; 95/242; 96/176; 96/177; 203/20; 210/188; 210/608; 435/812; 435/286.1; 435/286.5; 435/301.1
[58] Field of Search .............................. 202/264; 203/20; 210/608, 188; 95/242; 96/177, 176; 435/812, 291, 289

[56] References Cited

U.S. PATENT DOCUMENTS

| | | | |
|---|---|---|---|
| 2,405,138 | 8/1946 | Gates | 96/177 |
| 3,011,956 | 12/1961 | Smith et al. | 203/20 |
| 3,354,050 | 11/1967 | Rungaldier et al. | 435/812 |
| 3,649,557 | 3/1972 | Freedman et al. | 96/177 |
| 4,085,007 | 4/1978 | Hawkins | 435/812 |
| 4,373,024 | 2/1983 | Hunt | 95/242 |
| 4,610,701 | 9/1986 | Hoffman | 96/177 |
| 4,987,082 | 1/1991 | Gallagher | 435/812 |
| 4,997,660 | 3/1991 | Wittler | 435/812 |

FOREIGN PATENT DOCUMENTS

| | | |
|---|---|---|
| 39-26041 | 11/1964 | Japan . |
| 39-29800 | 12/1964 | Japan . |
| 46-30786 | 9/1971 | Japan . |
| 51-35470 | 3/1976 | Japan . |
| 51-142585 | 12/1976 | Japan . |

OTHER PUBLICATIONS

Patent Abstracts of Japan, vol. 12, No. 148 (C–493) (2995), May 7, 1988, JP-A-62 262985, Nov. 16, 1987.
Patent Abstracts of Japan, vol. 4, No. 151 (C–28)(633), Oct. 23, 1980, JP-A-55 097284, Jul. 24, 1980.
Database WPI, Derwent Publications Ltd., AN 308851, JP-A-51 142 585, Dec. 9, 1976.

Primary Examiner—Wilbur Bascomb, Jr.
Attorney, Agent, or Firm—Oblon, Spivak, McClelland, Maier, & Neustadt

[57] ABSTRACT

An apparatus and method for defoaming aerobic fermentation cultures is provided, where the amount of liquid culture medium used is greater than that in conventional aerobic cultures (70% or more of the total capacity of the culture tank) without lowering the productivity of the intended, desired product. In the present apparatus and method, a device for separating vapor from liquid of a foam is in fluid communication with the fermentation tank, a device for condensing residual liquid of the vapor received from the separating device is in fluid communication with the separating device, and a sensor for detecting foams is provided in a location along the fluid communication pathway. In the defoaming apparatus, an optional defoaming device is provided, which may be based on either a rotary body rotating at a high speed by use of an electric motor which beats the foams, or on a centrifugal atomizer. The defoaming device may be provided between the vapor-liquid separating device and the condensing device.

10 Claims, 4 Drawing Sheets

APPARATUS FOR DEFOAMING AND CONTROLLING AEROBIC CULTURE FERMENTATION

BACKGROUND OF THE INVENTION

1. Field of the Invention

The present invention concerns a defoaming apparatus for use in the aerobic fermentative production of useful chemical and biological substances, as well as methods of defoaming and controlling aerobic fermentation cultures in the production of useful chemical and biological substances.

2. Discussion of the Background

In the fermentation industry, aerobic microorganisms are generally used for producing useful chemical and biological substances. Such aerobic microorganisms are cultured in a culture tank or fermentation tank, containing a liquid culture medium. Where a large amount of air is blown into a culture liquid, foams are expected to be generated. If the generated foams are not reduced or eliminated during culturing, the tank is filled with the scum of the foams, causing the scum to overflow into the exhaust system of the culture tank. In particular, if the amount of the culture liquid is relatively large compared with the capacity of the culture tank (approximately 70% or more of the tank capacity), then the possibility of scum or foam overflowing into the exhaust system increases dramatically.

In general, methods of defoaming are employed for the purpose of inhibiting foaming during fermentative culturing. In one method, a foam detector is provided in the culture tank, and a defoaming agent (a surfactant or silicone) is added to the tank (for instance, see C. L. Kroll et al.; I.E.C., 48, 2190 (1956)). In accordance with this method, however, the amount of defoaming agent in the tank is difficult to control. Therefore, productivity using this method is low.

Another defoaming method employs defoaming blades disposed above the stirring blades in the fermentation tank, to act on areas or surfaces of vapor (air)-liquid contact. In general, as fermentation progresses, components such as nutrient sources and pH-altering substances are added to the culture medium. In accordance with the defoaming method employing defoaming blades, however, the scum of the foams generated is merely pushed back into the medium as the amount of the culture liquid in the culture tank increases. Using only the device of this method, complete control of the scum surface of the foams generated is impossible.

In fermentative production operations typically used at the commercial plant level, a combined method is used in which the scum surface of the generated foams is detected with an electrode sensor disposed in the upper area of the culture tank (above the surface of the culture medium), and a surfactant and a silicone chemical agent are added to the tank as defoaming agents. The scum surface of the generated foams is thus retained in the lower portion of the culture medium below the defoaming blades (for instance, see Japanese Patent Publication No. 46-30786, and FIG. 4 herein).

In accordance with this combined method, however, the amount of the culture liquid to be charged into the culture tank is limited due to the defoaming blades. Increasing the amount of culture liquid increases the amount of power necessary to turn the stirring and defoaming blades. Generally, when the amount of culture liquid increases to that amount requiring about three times the original power to turn the blades, vigorous foaming occurs. At this point, the power necessary to turn the blades exceeds the maximum capacity of conventional motors. As a result, the space in the upper area of the culture tank is not utilized efficiently. Further, the product output and/or the efficiency of production as a function of energy input is reduced, compared with methods which expend energy to rotate only the stirring blades.

Other defoaming means include a method of removing the scum of foams by providing a separate rotor in the upper area of the culture tank (above the surface of the liquid culture medium), and rotating the rotor by an electric motor at a high speed to remove the scum of the foams generated during fermentation (for instance, see I. H. Muller; Process Biochem., 37 (June, 1972)); and a defoaming tank having horizontally rotating blade propellers disposed at the exhaust outlet (see Japanese Utility Model Publication No. 39-36996).

The methods providing a separate rotor or horizontally rotating blade propellers have a high power cost for the electric motor when the culture tank is of sufficiently large scale. The amount of the culture liquid therein is large, proportionally creating even more foam, thus limiting the allowable amount of culture liquid in the fermentation tank.

Another defoaming method breaks foams generated in a fermentation or culture tank against a cyclone, a baffle, or the like, positioned in a "loop" external to the tank. The culture liquid from which the generated foams have been removed is then re-circulated into the culture tank (see Japanese Patent Publication Nos. 39-29800 and 39-26041). In accordance with this method, however, complete defoaming is impossible. Culture liquid to be re-circulated still contains significant amounts of foam. As a result, the gas hold-up in the culture liquid is not lowered, and the amount of the culture liquid charged into the culture tank cannot be increased, compared to the previously discussed methods. Thus, productivity is also low, as is its utility as a practical production process.

An improved defoamer introduces culture liquid and foams generated therein into one cyclone located externally to the fermentation tank, and the defoamed liquid is then recycled into the culture tank from the top and is brought into contact with a gas fed into the tank from the bottom by countercurrent contact (see Japanese Patent Laid-Open Application No. 51-142585). Using this device, however, sterilization of the defoamer is difficult during fermentative production processes, and the feed lines of the device are often clogged due to solids or the like in the culture liquid. Thus, this device is also difficult to use in an actual production process.

A defoaming method is also known in which a part of a culture liquid is "sprinkled" (see Japanese Patent Laid-Open Application No. 51-35470). However, the "sprinkling" method is complicated by microbial contamination of the sprinkling device, and complete defoaming is impossible. Thus, the desired effects of the method are not realized.

A defoaming device to be operated by discharging is also known (see Japanese Patent Laid-Open Application Nos. 55-15639). The device is useful on a small scale; for example, less than 1 kiloliter. However, on a large scale (e.g., that used for mass production), problems arise and the equipment for the device is complicated. Thus, the discharging device is not practical.

The above-mentioned known defoaming devices and methods of controlling the scum surface of foams are not applicable to practical production processes. For example, use of amounts of liquid culture media up to 60–70% (or more) of the total capacity of the culture tank is impossible without reducing the yield of the intended products.

SUMMARY OF THE INVENTION

Accordingly, one object of the present invention is to provide a novel defoaming apparatus which permits efficient fermentation wherein the amount of the culture liquid in the culture tank may be from 60% to 70% or more of the capacity of the fermentation tank.

Another object of the present invention is to provide a novel defoaming apparatus and method which does not adversely affect the yield of the desired chemical or biological product(s).

Another object of the present invention is to provide a novel defoaming apparatus and method in which fermentation may be conducted using a minimal amount of a defoaming agent without contaminating the culture tank with microbes.

Another object of the present invention is to provide a novel defoaming apparatus and method which defoams and controls removal of foams generated during fermentation cultures.

These and other objects which will become apparent during the course of the following detailed description of the preferred embodiments has been realized by a defoaming apparatus for an aerobic culture fermentation tank, comprising:

a means for separating vapor from liquid of a foam, in fluid communication with said fermentation tank, a means for condensing residual liquid of said vapor received from said separating means, in fluid communication with said separating means, a means for recirculating the liquid from said separating means and the condensed residual liquid, said recirculating means being in fluid communication with said fermentation tank, said separating means and said condensing means, and a sensor for detecting foams, located in the fluid communication pathway from said separating means to said recirculating means.

DETAILED DESCRIPTION OF THE PREFERRED EMBODIMENTS

Figure 1A:
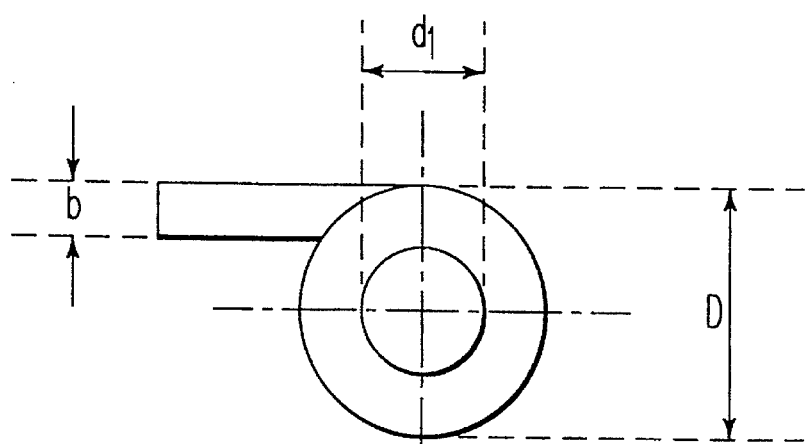
FIG. 1 shows a vapor-liquid separating means and mist separating means.

The present Inventors have found a novel defoaming method and apparatus, in which the scum of foams generated in a fermentation culture tank is reduced or eliminated without adversely affecting the productivity of the fermentation process. The present invention encompasses a two-stage apparatus or device, comprising a means for separating vapor from liquid in a foam, such as a cyclone or the like, and a means for condensing residual liquid from the separated vapor in fluid communication with the separating means. The separated foam vapor contains a mist having fine liquid particles suspended in the vapor. These liquid particles are condensed into a bulk liquid, which is recirculated back to the fermentation culture tank.

A sensor is provided, for example, in one or more of (i) the body of the mist separating means, (ii) the inlet line thereto, or (iii) the line(s) for recirculating the defoamed culture liquid to the culture tank. Thus, when the foam overflows from the vapor-liquid separating means, the foam is detected by the sensor. When the sensor detects the presence of foam, a signal is created, and sent to a means for adding defoaming agent to the culture tank. A defoaming agent is then added to the culture tank in response to the signal from the sensor, thus preventing the foams from overflowing out of the exhaust system, and thus controlling the foams, minimizing the amount of defoaming agent and maximizing the efficiency of the fermentation.

In addition, the present Inventors also have found that further providing the defoaming apparatus of the present invention with a mechanical defoaming means in which either (1) the generated foams are beaten with a rotor, the rotor being driven by a separate electric motor at a high speed, or (2) the foams are atomized by centrifugal atomization, enhances the defoaming effects of the apparatus and can result in improved defoaming. A "high speed" means the revolution rate or number sufficient to maintain the height of the foam at a constant level in the apparatus (for example, at the level above the surface of the liquid culture medium corresponding to the position of the above the mechanical defoaming means). Preferably, the mechanical defoaming means is located between the vapor-liquid separating means and the mist separating (condensing) means.

Preferably, the present means for separating foam vapor from foam liquid is located at the exhaust outlet of the device fermentation tank. The "mist separating means" (means for condensing residual liquid present in the separated foam vapor) is preferably positioned at the vapor outlet of the vapor-liquid separating means, and at least one sensor for detecting foams is provided in at least one location in the fluid communication pathway between the separating means up to and including the recirculating means. Particularly preferably, the sensor is placed in a location selected from the inlet line between the vapor-liquid separating means and the mist separating means, the recirculation line and the body of the residual liquid condensing means.

The present defoaming apparatus may further comprise a mechanical defoaming device provided between the vapor-liquid separating means and the mist separating means. The mechanical defoaming device is preferably either a rotary body 23 placed in a location permitting the rotary body to beat the foams, or a means for centrifugal atomization of the foams. Preferably, the rotary body 23 is rotated by means of an electric motor.

In addition, the present invention further provides a method of defoaming and controlling foams in aerobic fermentation cultures, comprising:

culturing an aerobic microorganism in a fermentation tank containing a suitable medium for a length of time sufficient to produce a foam, separating vapor from liquid in a portion of said foam, condensing residual liquid from said vapor, detecting foam produced in excess of the portion of foam in which vapor is separated from liquid, adding a defoaming agent in response to said detecting, and recirculating the separated liquid and condensed residual liquid to said fermentation tank.

Any "portion" of foam, from more than zero percent to 100%, may have its vapor components separated from its liquid components in the present separating step. Excess foam (i.e., that amount of foam not having its constituent vapor separated from its constituent liquid) overflowing the separating means is then detected by the sensor, which triggers a signal to a means for adding defoaming agent to the culture medium in the tank. Suitable adding means may include a defoaming agent feed or inlet line equipped with an appropriately controlled valve, in fluid communication with the culture tank.

Further, the steps of the present method are not necessarily intended to be performed consecutively. Fermentation is a continuous process, and as a result, the steps of the present process may be performed as needed, in response to the volume of foam in the tank and defoaming apparatus, the volume or amount of culture medium, the location of the sensor(s), the volume of liquid separated or condensed, etc. Preferably, each of the steps of the present process are performed as needed in response to the corresponding volume of foam and/or liquid, and are not performed if not necessary. For example, defoaming agent preferably is not added unless the sensor detects the presence of foam. Likewise, if liquid is separated from vapor in the foam, or subsequently condensed from the vapor, but no foam per se is present in the apparatus, the liquid may be recirculated without performing the detecting step prior to recirculating.

Aerobic fermentation cultures to which the present invention particularly applies include those fermentation cultures of aerobic microorganisms used to produce amino acids, nucleic acids, sugars and the like, but is not limited thereto. For example, the present defoaming method can be used in the fermentative production of aspartame. Examples of aerobic microorganisms include those belonging to the genera *Arthrobacter, Bacillus, Brevibacterium, Corynebacterium, Escherichia, Flavobacterium, Klebsiella, Lactobacillus, Microbacterium, Micrococcus, Mycobacterium, Nocardia, Proteus, Pseudomonas, Rhodococcus, Serratia, Staphylococcus, Streptococcus, Streptomyces* and *Thermus*. Examples of the amino acids produced by cultures of aerobic microorganisms include naturally occurring amino acids, such as L-glutamic acid, L-lysine, L-arginine, L-aspartic acid, L-asparagine, L-phenylalanine, L-tyrosine, L-tryptophan, L-leucine, L-isoleucine and L-histidine. Examples of nucleic acids produced by aerobic fermentation cultures include adenosine, cytosine, guanosine, thymine, uracil, etc. An example of a sugar produced by aerobic fermentation cultures includes D-ribose. The method of culturing the microorganism(s) used to produce the desired product(s) above may be of any type; for example, batch culture, flow addition culture, continuous culture, etc. The culture conditions may be those conventionally used in conventional culture methods.

Figure 1B:
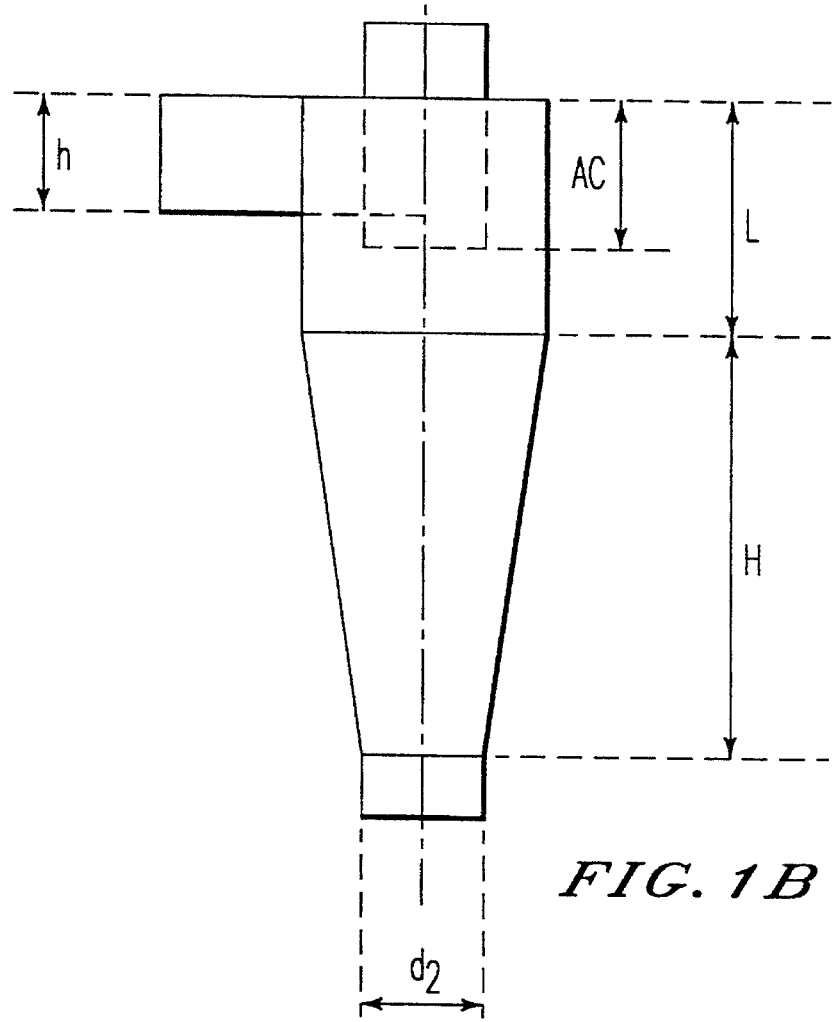

One non-limiting embodiment of the vapor-liquid separating means used in the present invention employs a cyclone having the shape shown in FIG. 1 and dimensions represented by the following formulae:

$b=D/5$ $h=D/2$ $d_1=2D/5$ $d_2=8D/25$ $L=D$ $H=2D$ $Ac=3D/5$ where:

D is the cyclone diameter;
$d_1$ is the diameter of the cyclone gas exit duct;
b is the width of the rectangular cyclone inlet duct;
h is the height of the rectangular cyclone inlet duct;
$d_2$ is the diameter of the cyclone liquid exist duct;
L is the length of the cylindrical chamber of the cyclone;
H is the length of the conical chamber of the cyclone; and
Ac is the length of the overflow pipe.

Two or more vapor-liquid separating means overlaid with each other (e.g., in a series) may be used to attain the same effect.

A non-limiting example of the mist-separating means suitable for use in the present invention is a cyclone having the shape shown in FIG. 1 and dimensions represented by the following formulae:

$b=D/5$ $h=D/2$ $d_1=2D/5$ $d_2=8D/25$ $L=D$ $H=2D$ $Ac=3D/5$ where b, h, $d_1$, $d_2$, L, d, H and Ac are as defined above. The cyclone of the vapor-liquid separating means and the cyclone of the mist separating means may differ in dimensions. Preferably, the dimensions of each cyclone differ in a manner consistent with the intended purpose of each of the vapor-liquid separating means and the mist separating means. A dashing-type Bergius-Müller's apparatus is also suitable for the vapor-liquid separating means and the mist separating means.

Sensors suitable for use in the present invention include an ultrasonic flow meter, an electrostatic volume flow switch, an electromagnetic flow meter, an optical flow switch, a heat-diffusing flow switch and an electrode sensor. Preferred sensors include an optical flow switch sensor and a heat-diffusing flow switch sensor.

The mechanical defoaming means, employing either a rotary body rotating at a high speed by means of an electric motor, or which centrifugally atomizes foams, is exemplified by the FOAMJET device, manufactured by EKATO Co. of Germany.

Figure 2:
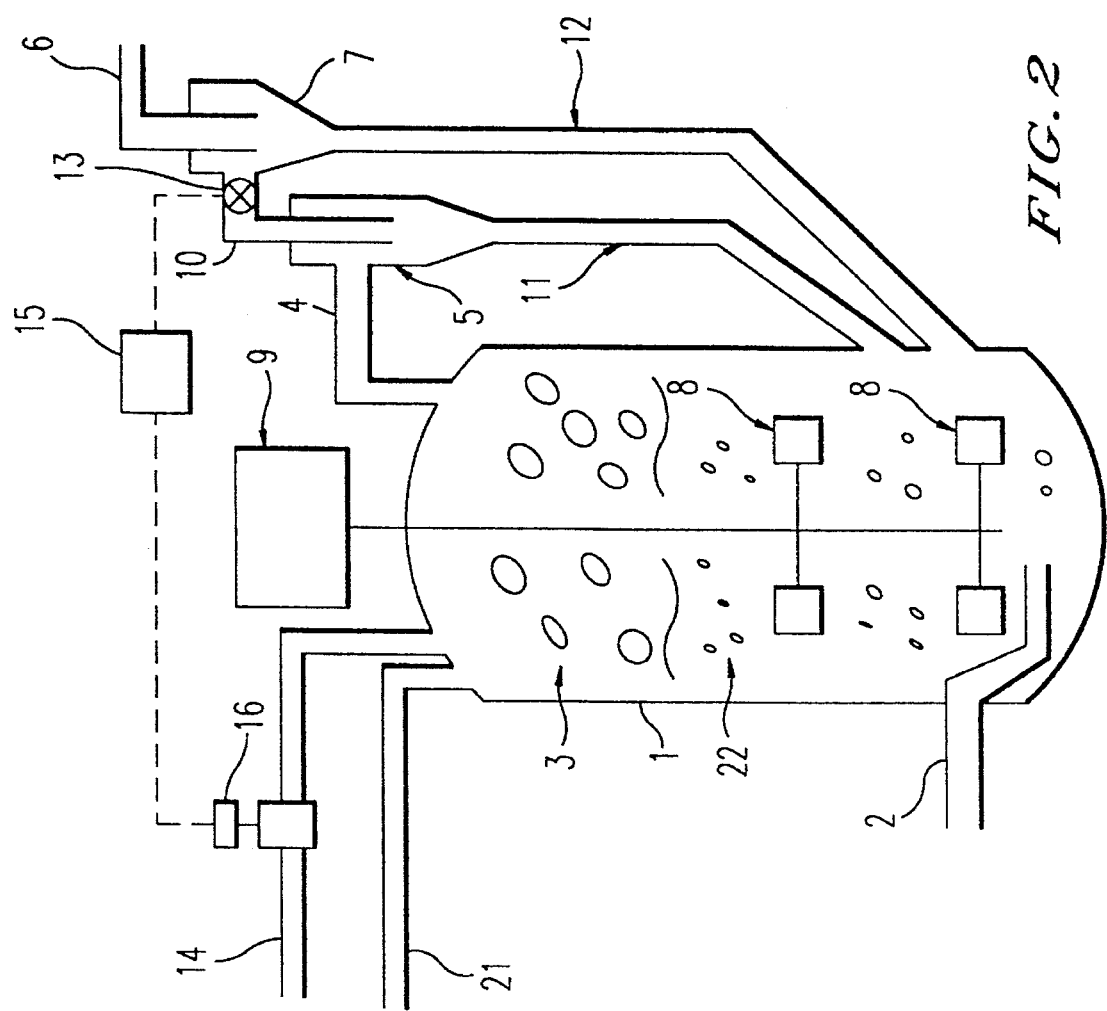
FIG. 2 shows a fermentation apparatus exemplifying the present invention.
Figure 3:
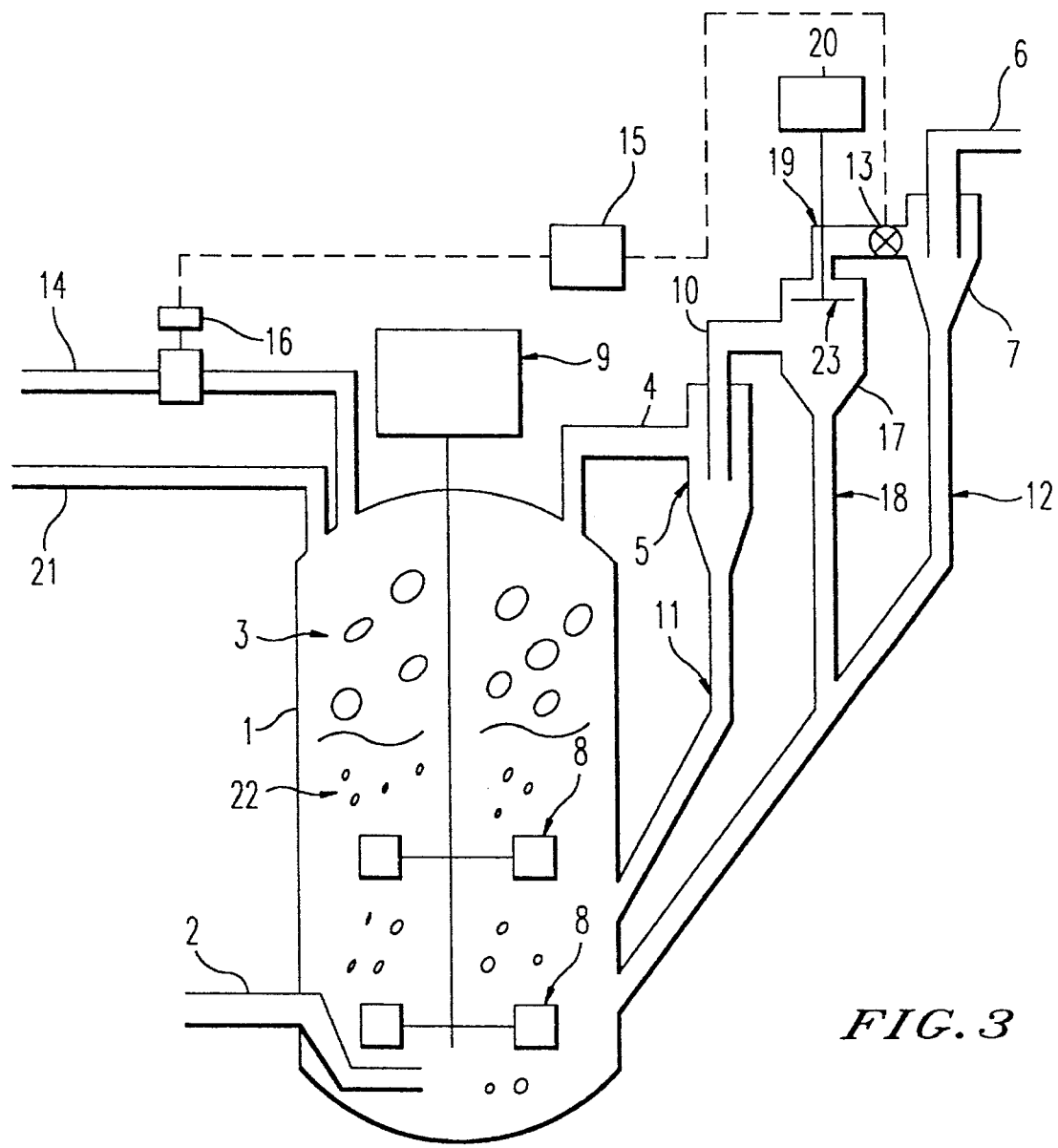
FIG. 3 shows a second fermentation apparatus exemplifying the present invention.

Aerobic fermentation culture apparatuses for use in the present invention are shown in each of FIGS. 2 and 3.

FIG. 2 is a longitudinal sectional view of a culture apparatus as used in carrying out Examples 1 and 3 described below. A culture tank 1 is filled with a liquid culture medium 22, and an air feeding duct 2 is disposed at the bottom of the tank 1. An exhaust duct 4, which removes foams 3 formed in the culture tank 1, is disposed at the top of the tank 1. A cyclone 5 is connected at one end to the exhaust duct 4, and the other end of the cyclone 5 is connected to the culture tank 1 via a liquid recirculating duct 11. (The term "connected to" means to be in fluid communication with.) Cyclone 5 is equipped with an exhaust duct 10, connected to a second cyclone 7. Cyclone 7 and the culture tank are connected with each other via a second recirculating duct 12. The recirculating ducts 11 and 12 may, of course, be connected with each other. Cyclone 7 is equipped with an exhaust duct 6. Fermentation tank 1 is equipped with a stirring device comprising stirring blades 8 and a stirring motor 9. A foam sensor 13 is positioned in exhaust duct 10, between cyclone 5 and cyclone 7. The tank 1 is further equipped with an inlet line 14 for adding defoaming agent to the culture tank 1 as needed, in response to signals from foam sensor 13 processed by defoaming agent addition controller 15, connected electrically to foam sensor 13 and defoaming agent valve 16, placed in defoaming agent inlet line 14. The foam sensor 13 may be attached to the exhaust duct 10 and/or the recirculating duct 12.

Excess air blown into the bottom of the culture tank 1 and the foams 3 generated by the action of the stirring blades are removed through the exhaust duct 4 provided in the top of the tank 1, and are subsequently introduced into the cyclone 5, where they are, at least in part, defoamed. The defoamed liquid is then recirculated to the culture tank 1. However, if the volume of the foam 3 exceeds the volume of exhaust duct 4 and cyclone 5, the foam 3 overflows into the exhaust duct 10 of the cyclone 5. When foam sensor 13 disposed in exhaust duct 10 and/or recirculating duct 12 detects the foams, a defoaming agent is added in response to a signal triggered by detection of the foam 3 by foam sensor 13. When the foam sensor no longer detects foam 3, the signal is stopped and addition of the defoaming agent is also subsequently stopped. This defoaming process is repeated as necessary until the culture process is completed.

FIG. 3 shows a culture apparatus in which a mechanical defoaming means is provided between the vapor-liquid separating means 5 and the mist separating means 7.

A tank 17 equipped with a mechanical defoaming means is connected to exhaust duct 10 of the cyclone 5, and the tank 17 and the culture tank 1 fluidly communicate with each other via a recirculating duct 18. The tank 17 is equipped with an exhaust duct 19, connected to a cyclone 7. Cyclone 7 and the culture tank 1 are connected with each other via recirculating duct 12, joined to recirculating duct 18. All of the recirculating ducts 11, 12 and 18 may optionally be connected with each other. A foam sensor 13 may be provided in the exhaust duct 19, the recirculating duct 12, or in both of them. A mechanical defoaming means 20 is provided at the top of tank 17.

The culture apparatus of FIG. 3 differs from that of FIG. 2 in that the foams 3 overflowing from the tank 17 are defoamed by the mechanical defoaming means 20 in the apparatus of FIG. 3. When the foam 3 overflows from the tank 17, overflowing foam is detected by the foam sensor 13 positioned in exhaust duct 19, then a defoaming agent is added in response to a signal from sensor 13. When the foam sensor no longer detects the foam, then addition of the defoaming agent is stopped. This defoaming process is repeated as necessary until the end of the culture process.

By controlling the foams by the use of the defoaming apparatus of the present invention, use of defoaming blades is unnecessary. Energy input, needed for the defoaming blades, is eliminated, reducing total energy input. In addition, the risk of contamination of the culture system by microbes is minimized, and operation of the culture process may be conducted without adding excess defoaming agent into the culture tank. In the method exemplified by FIG. 2, the amount of liquid culture may be elevated up to 73–80% of the total capacity of the culture tank. In the method of FIG. 3, surprisingly, the amount of liquid culture may be elevated up to 76–86% of the total capacity of the culture tank, although the energy input subsequently increases.

Other features of the present invention will become apparent in the course of the following descriptions of exemplary embodiments which are given for illustration of the invention, and are not intended to be limiting thereof.

EXAMPLE 1

Using *Brevibacterium lactofermentum* ATCC 13869 (a glutamic acid-producing bacterium), glutamic acid fermentation was conducted in the culture apparatus of FIG. 2 (total capacity of culture tank: 300 kl, air stream rate at the air inlet of the cyclone: 15 to 30 m/sec). A culture medium was prepared by adding the additives shown in Table 1 below to 140 kl of molasses having a sugar concentration of 80 g/liter. To the culture medium, about 10 kl of previously cultivated *Brevibacterium lactofermentum* ATCC 13869 was inoculated. The mixture was then cultivated at 31.5° C. under aerial stirring, maintaining the pH of the medium at 7.5 with ammonia gas (introduced into the medium through the air duct as needed). When the sugar concentration in the medium dropped below 3%, molasses having a sugar concentration of 300 g/liter was added to the medium little by little, maintaining the sugar concentration between 2 and 4% during the course of cultivation. When the amount of the cells cultivated reached a predetermined level, a surfactant was added to the medium (0.6% of TWEEN 60). A polypropylene glycol ("PPG"; AZ20R, manufactured by Nippon-Yushi Co., Japan) was supplied to the culture tank as a defoaming agent.

TABLE 1

| Additive | Amount |
| --- | --- |
| Potassium Phosphate | 3 g/liter |
| Urea | 4 g/liter |
| Magnesium Sulfate 7-Hydrate | 0.5 g/liter |
| Ferrous Sulfate 7-Hydrate | 20 mg/liter |
| Manganese Sulfate 4-Hydrate | 20 mg/liter |
| Thiamine Hydrochloride | 200 µg/liter |
| Soybean Protein Hydrolysate (total nitrogen content: 40 g/liter) | 30 µg/liter |
| Biotin | 30 µg/liter |

Five hours after initiation of the cultivation, foaming became vigorous, whereupon foams overflowed into the cyclone of the vapor-liquid separating means. The foams not fully broken in the cyclone overflowed into the exhaust duct of the vapor-liquid separating cyclone, and were detected by the foam sensor. In response thereto, defoaming agent was added to the tank in an amount sufficient to stop foam from overflowing into the cyclone of the vapor-liquid separating means, thus temporarily controlling the surface of the scum of the foam.

About 15 hours after initiation of cultivation, foaming again became vigorous, whereupon foams formed temporarily overflowed to the cyclone from the exhaust outlet of the culture tank. The foams not well-controlled in the cyclone of the vapor-liquid separating means overflowed to the mist separating cyclone, whereupon the foam sensor instantaneously detected the foams, and defoaming agent was subsequently added to the tank in an amount sufficient to stop foam from overflowing into the cyclone.

Subsequently, the defoaming agent was added in a manner dependent on the amount of previously added defoaming agent. Generally, addition of the defoaming agent was repeated a few times each hour.

After cultivation for 26 hours, control of the level of the scum of the foams formed became difficult. Addition of the sugar source was stopped, and the cultivation process was terminated. The final amount of the culture liquid reached 240 kl, and 86 g/liter of glutamic acid was obtained.

As a result of the process carried out as above, the fermentative production of glutamic acid was conducted without overflow of the culture liquid from the exhaust outlet of the mist-separating cyclone, even though the amount of the culture liquid was between 73 and 80% of the capacity of the culture tank.

EXAMPLE 2

In the same manner as Example 1, cultivation of *Brevibacterium lactofermentum* ATCC 13869 was conducted in the culture apparatus of FIG. 3 to produce glutamic acid. A culture medium was prepared by adding the additives shown in Table 1 above to 140 kl of molasses having a sugar concentration of 80 g/liter. To this medium, about 10 kl of previously cultivated Brevibacterium lactofermentum ATCC 13869 was inoculated. The culture was then cultivated at 31.5° C. under aerial stirring, maintaining the pH of the medium at 7.5 with ammonia gas. When the sugar concentration in the medium dropped below 3%, molasses having a sugar concentration 300 g/liter was added thereto little by little to maintain the sugar concentration between 2 and 4% during the course of cultivation. When the amount of the cells cultivated reached a predetermined level, a surfactant was added to the medium (TWEEN 60; 0.6% of the medium). A PPG compound was supplied to the culture tank as a defoaming agent.

Five hours after initiation of the cultivation, foaming became vigorous, whereupon foams overflowed into the vapor-liquid separating cyclone, and the foams not fully broken in the cyclone overflowed into the mechanical defoaming means (the FOAMJET device, manufactured by EKATO Co. of Germany) provided in the small tank between the vapor-liquid separating cyclone and the mist-separating cyclone, where they were subsequently defoamed. The level of the scum of the foams was temporarily controlled by the mechanical defoaming means. About 15 hours after initiation of the cultivation, foaming again became vigorous, whereupon foams overflowed into the vapor-liquid separating cyclone from the exhaust outlet of the culture tank. The foams not well-controlled by the mechanical defoaming means overflowed to the mist-separating cyclone, whereupon the foam sensor instantaneously detected the foams. Subsequently, defoaming agent was automatically added in an amount sufficient to stop foam from overflowing into the cyclone in response to the sensor detecting the foams. After a while, the amount of foam again increased, overflowing into the mist-separating cyclone, whereupon addition of the defoaming agent was repeated in response to the detection of the foam by the sensor.

After cultivation for 27 hours, control of the amount of the foam became difficult. Addition of the sugar source was stopped, and the cultivation process was termination. The final amount of the culture liquid reached 258 kl, and 90 g/liter of glutamic acid was obtained.

COMPARATIVE EXAMPLE 1

Figure 4:
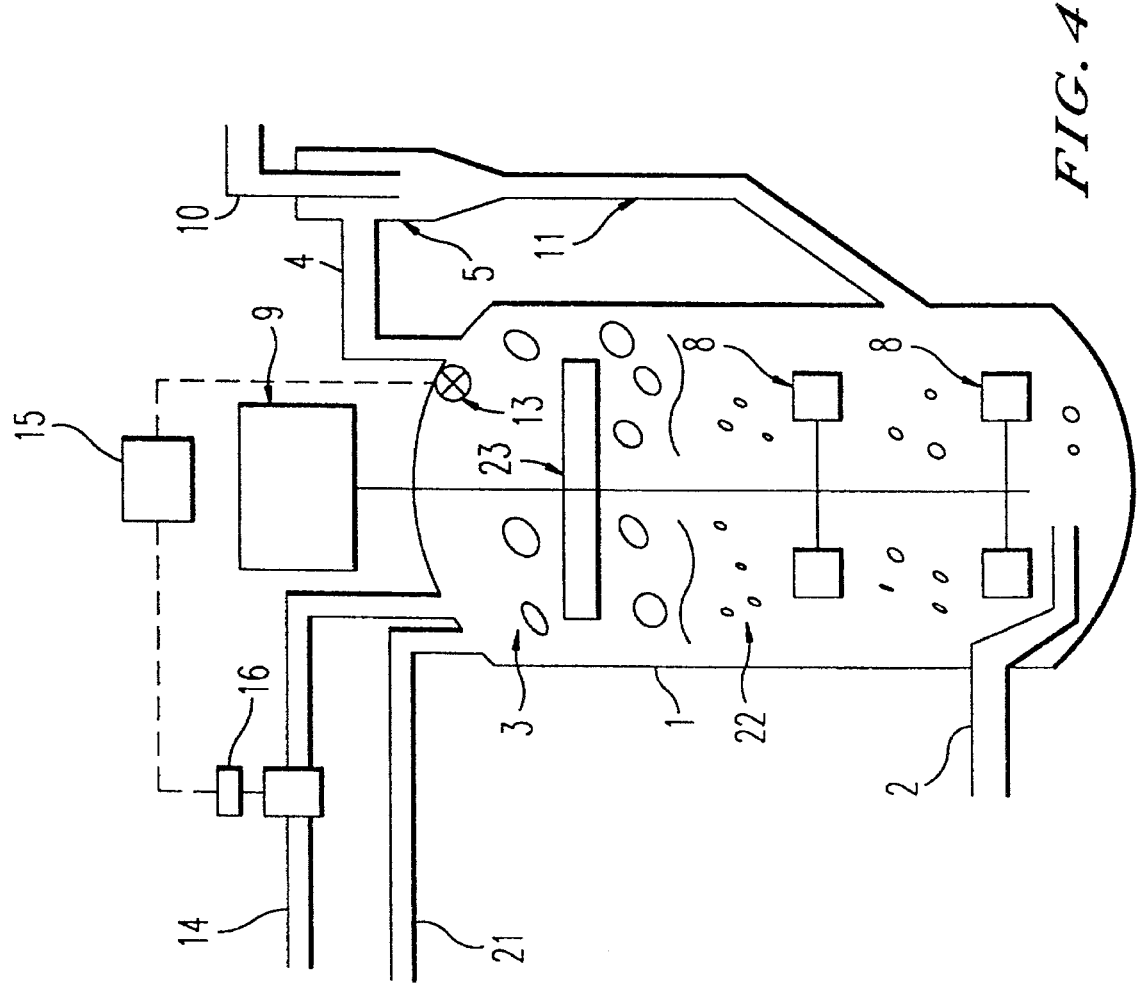
FIG. 4 shows a fermentation apparatus used in the Comparative Examples hereinbelow, exemplifying a prior defoaming method.

A culture device shown in FIG. 4, in which large-sized defoaming blades 23 are disposed at the top of the stirring shaft of the fermentation tank 1, was used to fermentatively produce glutamic acid. This experiment was conducted to compare with the processes of Examples 1 and 2.

The comparative defoaming device comprises an electrode type sensor 13 at the top of the fermentation tank, having a mechanism which adds a defoaming agent to the tank when the sensor detects foams.

Using the fermentation apparatus of FIG. 4, cultivation of *Brevibacterium lactofermentum* ATCC 13869 was conducted under the same conditions as those employed in Example 1, using molasses having the same sugar concentration as that of Example 1 as the sugar source. Up to 14 hours after initiation of the cultivation, defoaming agent was occasionally added to the tank. After 14 h, however, the frequency of addition of the defoaming agent increased. Finally, after cultivation for 24 hours, the amount of culture liquid increased to a level requiring about three times the original stirring energy, resulting in vigorous foaming. As a result, operation of the device became impossible, due to a requirement for agitation energy in the fermentation tank greater than the maximum capability of the corresponding motor. The final amount of the culture liquid was 210 kl, and 78 g/liter of glutamic acid was obtained.

The results obtained in Examples 1 and 2 and Comparative Example 1 are summarized in Table 2 below. The yield was calculated by the following formula:

$$\text{Yield (\%)} = \frac{\text{amount of glutamic acid (kg)}}{\text{amount of sugar (kg)}} \times 100\%$$

TABLE 2

| Items for Comparison | Comparative Example 1 | Example 1 | Example 2 |
| --- | --- | --- | --- |
| Final amount of culture liquid (kl) | 210 | 240 | 258 |
| (Final amount of culture liquid)/(total capacity of culture tank) (%) | 70 | 80 | 86 |
| Concentration of L-glutamic acid formed (g/liter) | 78 | 86 | 90 |
| Relative amount of energy used (based on the amount used in Comparative Example 1) | 1 | 0.6 | 0.8 |
| Relative amount of defoaming agent used (based on the amount used in Comparative Example 1) | 1 | 1.1 | 0.9 |
| Cultivation Time (hr) | 28 | 29 | 30 |
| Yield (%) | 50.8 | 50.0 | 49.8 |

EXAMPLE 3

Cultivation of *Brevibacterium lactofermentum* FERM BP071 was conducted in the culture apparatus of FIG. 2 for production of L-phenylalanine. A culture medium was prepared by adding the additives shown in Table 3 below to 140 kl of molasses having a sugar concentration of 150 g/liter. To this mixture was inoculated about 10 kl of previously cultivated *Brevibacterium lactofermentum* FERM BP-1071, which was then cultivated at 30.0° C. under aerial stirring, maintaining the pH of the medium at 7.5 with ammonia gas as described in Example 1 above. When the sugar concentration in the medium dropped below 3%, molasses having a sugar concentration of 450 g/liter was added little by little, maintaining the sugar concentration between 2 and 4% during the course of cultivation. A silicon compound (TMA812 polydimethylsilicone oil, produced by Toshiba Silicon Co., Japan) was supplied to the tank as a defoaming agent.

TABLE 3

| Additive | Amount |
| --- | --- |
| Phosphoric Acid | 1 g/liter |
| Magnesium Sulfate 7-Hydrate | 0.5 g/liter |
| Manganese Sulfate 4-Hydrate | 10 mg/liter |
| Soybean Protein Hydrolysate (total nitrogen content: 40 g/liter) | 5 ml/liter |
| Biotin | 50 µg/liter |
| Thiamine Hydrochloride | 2 mg/liter |

TABLE 3-continued

| Additive | Amount |
| --- | --- |
| Tyrosine | 1 g/liter |
| Potassium Hydroxide | 0.7 g/liter |
| DL-methionine | 1 g/liter |

EXAMPLE 4

Cultivation of Brevibacterium lactofermentum FERM BP-071 was conducted in the culture apparatus of FIG. 3 for production of L-phenylalanine. A culture medium was prepared by adding the additives shown in Table 3 above to 40 kl of molasses having a sugar concentration of 150 g/liter. To this mixture was inoculated about 10 kl of previously cultivated *Brevibacterium lactofermentum* FERM BP-1071, which was then cultivated at 30.0° C. under aerial stirring, maintaining the pH of the medium at 7.5 with ammonia gas. When the sugar concentration in the medium dropped below 3%, molasses having a sugar concentration of 450 g/liter was added little by little to the medium to maintain the sugar concentration between 2 and 4% during the course of cultivation. The same silicon compound as example 3 was supplied to the tanks a defoaming agent.

COMPARATIVE EXAMPLE 2

The culture apparatus of FIG. 4, described above in Comparative Example 1, was used in this experiment. This experiment compares with the processes of Examples 3 and 4.

*Brevibacterium lactofermentum* FERM BP-1071 was cultivated in the fermentation apparatus of FIG. 4, under the same conditions as those employed in Example 3. A molasses having the same sugar concentration as that in Example 3 was used. The silicon compound of Example 3 was employed as a defoaming agent.

Results of Examples 3 and 4 and Comparative Example 2 are shown in Table 4 below.

TABLE 4

| Items for Comparison | Comparative Example 2 | Example 3 | Example 4 |
| --- | --- | --- | --- |
| Final amount of culture liquid (kl) | 207 | 220 | 228 |
| (Final amount of culture liquid)/(Total capacity of culture tank) (%) | 69 | 73 | 76 |
| Energy used (relative to Comparative Example 2, defined as 1) | 1.0 | 0.6 | 0.9 |
| Amount of defoaming agent used (relative to Comparative Example 2, defined as 1) | 1.0 | 1.2 | 1.1 |
| Cultivation Time (hr) | 96 | 98 | 99 |
| Yield (%) | 13.0 | 12.5 | 12.3 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An apparatus for defoaming an aerobic culture fermentation tank, comprising:

a first means for separating vapor from liquid of a foam, a second means for separating residual liquid of said vapor received from said first means for separating, in fluid communication with said first means for separating, a means for recirculating liquid from said first means for separating and condensed residual liquid from said second means for separating, said means for recirculating being in fluid communication with said first means for separating and said second means for separating, and a sensor for detecting foams, located between and in fluid communication with said first means for separating and said second means for separating.

2. The apparatus of claim 1, further comprising a rotary body in fluid communication with and located between said first means for separating and said second means for separating, said rotary body being rotated by an electric motor and said sensor being located between and in fluid communication with said rotary body and said second means for separating.

3. The apparatus of claim 1, further comprising a means for centrifugally atomizing foams, in fluid communication with and located between said first means for separating and said second means for separating, wherein said sensor is located between and in fluid communication with said means for centrifugally atomizing foams and said second means for separating.

4. The apparatus of claim 1, wherein said first means for separating comprises a cyclone.

5. The apparatus of claim 1, wherein said second means for separating comprises a mist-separating cyclone.

6. The apparatus of claim 1, wherein said first means for separating comprises a first cyclone and said second means for separating comprises a second cyclone.

7. The apparatus of claim 1, further comprising a means for adding defoaming agent to said tank, electrically connected to said sensor.

8. An aerobic culture fermentation system comprising: an aerobic culture fermentation tank and an apparatus for defoaming, said apparatus comprising a first means for separating vapor from liquid of a foam, a second means for separating residual liquid from vapor received from said first means for separating, in fluid communication with said first means for separating, a means for recirculating liquid from said first means for separating and separated residual liquid from said second means for separating, said means for recirculating being in fluid communication (1) with said first means for separating, (2) with said second means for separating and (3) with said aerobic culture fermentation tank, and a sensor for detecting foams, located between and in fluid communication with said first means for separating and said second means for separating.

9. The aerobic culture fermentation tank of claim 8, wherein said fluid communication between said tank and said first and second means for separating comprises an exhaust duct disposed at the top of said tank.

10. The aerobic culture fermentation tank of claim 8, further comprising a means for adding defoaming agent to said aerobic culture fermentation tank, said means for adding being electrically connected to said sensor and being in fluid communication with said aerobic culture fermentation tank.

* * * * *